(12) United States Patent
Heinz (10) Patent No.: US 7,789,895 B2
(45) Date of Patent: Sep. 7, 2010

(54) SACRAL RECONSTRUCTION FIXATION DEVICE

(75) Inventor: Eric S. Heinz, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 863 days.

(21) Appl. No.: 11/616,050

(22) Filed: Dec. 26, 2006

(65) Prior Publication Data

US 2008/0154306 A1 Jun. 26, 2008

(51) Int. Cl.
*A61B 17/70* (2006.01)
*A61B 17/88* (2006.01)

(52) U.S. Cl. ......................... 606/246; 606/305; 606/279

(58) Field of Classification Search .................. 606/60, 606/246, 250–279, 300–331; 403/76, 77
See application file for complete search history.

(56) References Cited

U.S. PATENT DOCUMENTS

| | | | |
|---|---|---|---|
| 4,800,874 A | 1/1989 | David et al. | |
| 5,108,397 A | 4/1992 | White | |
| 5,242,445 A | 9/1993 | Ashman | |
| 5,474,555 A * | 12/1995 | Puno et al. | 606/266 |
| 5,498,263 A * | 3/1996 | DiNello et al. | 606/292 |
| 5,534,002 A * | 7/1996 | Brumfield et al. | 606/278 |
| 5,575,791 A * | 11/1996 | Lin | 606/278 |
| 5,593,407 A | 1/1997 | Reis | |
| 5,643,264 A | 7/1997 | Sherman et al. | |
| 5,702,393 A * | 12/1997 | Pfaifer | 606/328 |
| 5,800,548 A * | 9/1998 | Martin et al. | 606/253 |
| 6,267,765 B1 | 7/2001 | Taylor et al. | |
| 6,309,390 B1 * | 10/2001 | Le Couedic et al. | 606/264 |
| 6,551,318 B1 * | 4/2003 | Stahurski | 606/252 |
| 6,558,390 B2 | 5/2003 | Cragg | |
| 6,635,059 B2 | 10/2003 | Randall et al. | |
| 2003/0125741 A1 * | 7/2003 | Biedermann et al. | 606/61 |
| 2003/0144665 A1 * | 7/2003 | Munting | 606/61 |

(Continued)

FOREIGN PATENT DOCUMENTS

DE 39 24 050 A1 1/1991

(Continued)

OTHER PUBLICATIONS

"International Search Report," International Application No. PCT/US2007/088489, May 8, 2008, European Patent Office, Rijswijk, Netherlands.

(Continued)

*Primary Examiner*—Eduardo C Robert
*Assistant Examiner*—Devanie Dufour (57) ABSTRACT

A sacral reconstruction fixation device aids in stabilizing the pelvis and the lumbar spine after a sacrectomy in cooperation with a spinal rod and transiliac rod. A pair of the fixation devices may be secured to respective ilia and respective spinal rods. The transiliac rod may be secured to both of the fixation devices. The fixation devices include first and second parts that are initially relatively rotatable about a common axis to aid in connecting the fixation devices to the spinal rod and transiliac rod. The body part is intended to be mated to the spinal rod, while the second part is intended to be mated to the transiliac rod. The fixation device's parts are subsequently locked against rotation and against longitudinal translation, advantageously both relative to each other and the rods.

32 Claims, 6 Drawing Sheets

U.S. PATENT DOCUMENTS

| | | |
|---|---|---|
| 2003/0195518 A1 | 10/2003 | Cragg |
| 2004/0092931 A1 | 5/2004 | Taylor et al. |
| 2004/0133202 A1* | 7/2004 | Suzuki et al. ................. 606/61 |
| 2004/0138661 A1* | 7/2004 | Bailey ......................... 606/61 |
| 2005/0113830 A1* | 5/2005 | Rezach et al. ................. 606/60 |
| 2005/0113831 A1* | 5/2005 | Franck et al. ................. 606/61 |
| 2005/0149019 A1* | 7/2005 | Sasing et al. ................. 606/61 |
| 2006/0064092 A1 | 3/2006 | Howland |
| 2006/0241591 A1 | 10/2006 | Biscup et al. |
| 2007/0049932 A1* | 3/2007 | Richelsoph et al. ........... 606/61 |
| 2007/0118121 A1* | 5/2007 | Purcell et al. ................. 606/61 |
| 2007/0156142 A1* | 7/2007 | Rezach et al. ................. 606/61 |
| 2007/0173817 A1* | 7/2007 | Sournac et al. ............... 606/61 |
| 2008/0262546 A1* | 10/2008 | Calvosa et al. .............. 606/250 |

FOREIGN PATENT DOCUMENTS

| | | | |
|---|---|---|---|
| EP | 786235 A2 | * | 7/1997 |
| EP | 1 192 910 A2 | | 4/2002 |
| EP | 1 402 828 A2 | | 3/2004 |
| FR | 2 781 359 A1 | | 1/2000 |
| FR | 2865375 | * | 7/2005 |
| WO | WO 02/053038 | * | 7/2002 |

OTHER PUBLICATIONS

Zileli, Mehmet et. al., "Surgical Treatment of Primary Sacral Tumors: Complications Associated with Sacrectomy." Neurosurgical Focus, Nov. 2003, pp. 1-8, vol. 15, Article 9.

* cited by examiner

SACRAL RECONSTRUCTION FIXATION DEVICE

BACKGROUND

The invention relates to a fixation device to aid in the stabilization of the pelvis and the lumbar spine after a sacrectomy.

Removal of the sacrum, while undesirable, is sometimes necessary. For example, a malignant or benign tumor may be found in the sacrum, and removal of the sacrum may be the best treatment option. However, the sacrum performs two structural functions: vertically supporting the spine and securing the ilia of the pelvis against relative lateral displacement. Thus, during a sacrectomy surgical procedure, a surgeon may find it desirable to install an artificial construct for performing these structural functions. Typically, such a construct is custom made and involves the use of rods anchored to the ilia via the Galveston technique and joined to other rods anchored to the vertebrae of the spine. Installing such a construct increases the complexity and time required for the surgical procedure.

While the above approach may be appropriate for some situations, there remains a need for alternative surgical methods and devices for stabilization of the pelvis and the lumbar spine after a sacrectomy, advantageously ones that are compact and easy to use.

SUMMARY

In one illustrative embodiment, a sacral reconstruction fixation device is provided for stabilization of the pelvis and the lumbar spine after a sacrectomy in cooperation with a spinal rod and transiliac rod. A pair of the fixation devices may be secured to respective ilia and respective spinal rods. The transiliac rod may be secured to both of the fixation devices. The fixation devices include first and second body parts that are initially relatively rotatable about a common axis to aid in connecting the fixation devices to the spinal rod and transiliac rod. The first body part is intended to be mated to the spinal rod, while the second body part is intended to be mated to the transiliac rod. The fixation device's body parts are subsequently locked against rotation and against longitudinal translation, advantageously both relative to each other and the rods. Additional embodiments and related methods are also disclosed. For example, a convexly curvate body having a central bore therethrough of variable size may be disposed in the second body to aid in joining to the transiliac rod; the fixation device may also accept a second transiliac rod; and/or the first body may be allowed to have selectively lockable polyaxial motion relative to the iliac screw anchoring the first body to the ilia. The various disclosed aspects and embodiments may be used alone or in any combination.

DETAILED DESCRIPTION

Figure 1:
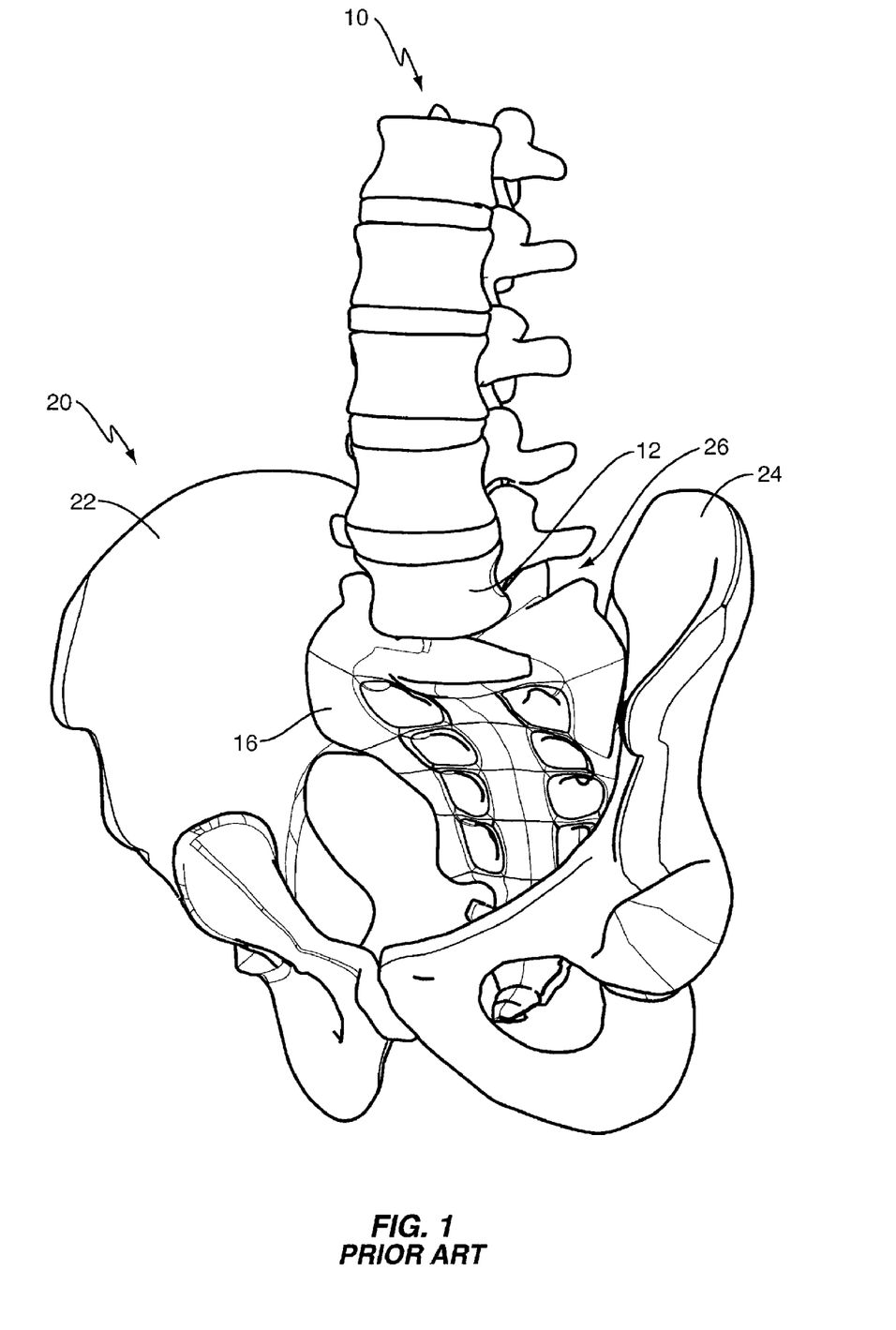
FIG. 1 shows a human pelvic girdle and partial spinal column.

The sacrum 16 is an inferior portion of the spinal column 10 that helps join the spinal column 10 to the pelvic girdle 20. The sacrum 16, in a healthy spine, provides a base that vertically supports the remainder of the spinal column 10 and typically directly supports the vertebra 12 in the lumbar region know as the L5 vertebra. In addition, the sacrum 16 helps maintain the pelvic girdle 20 against collapse. In particular, the sacrum 16 is disposed in the gap 26 between the right and left ilia 22,24, and helps keep the posterior portions of the ilia 22,24 spaced from one another. As indicated above, it is sometimes necessary or desirable to remove the sacrum 16 for a variety of reasons. Illustrative embodiments of the present invention provide stabilization of the pelvis and the lumbar spine after a sacrectomy.

Figure 2:
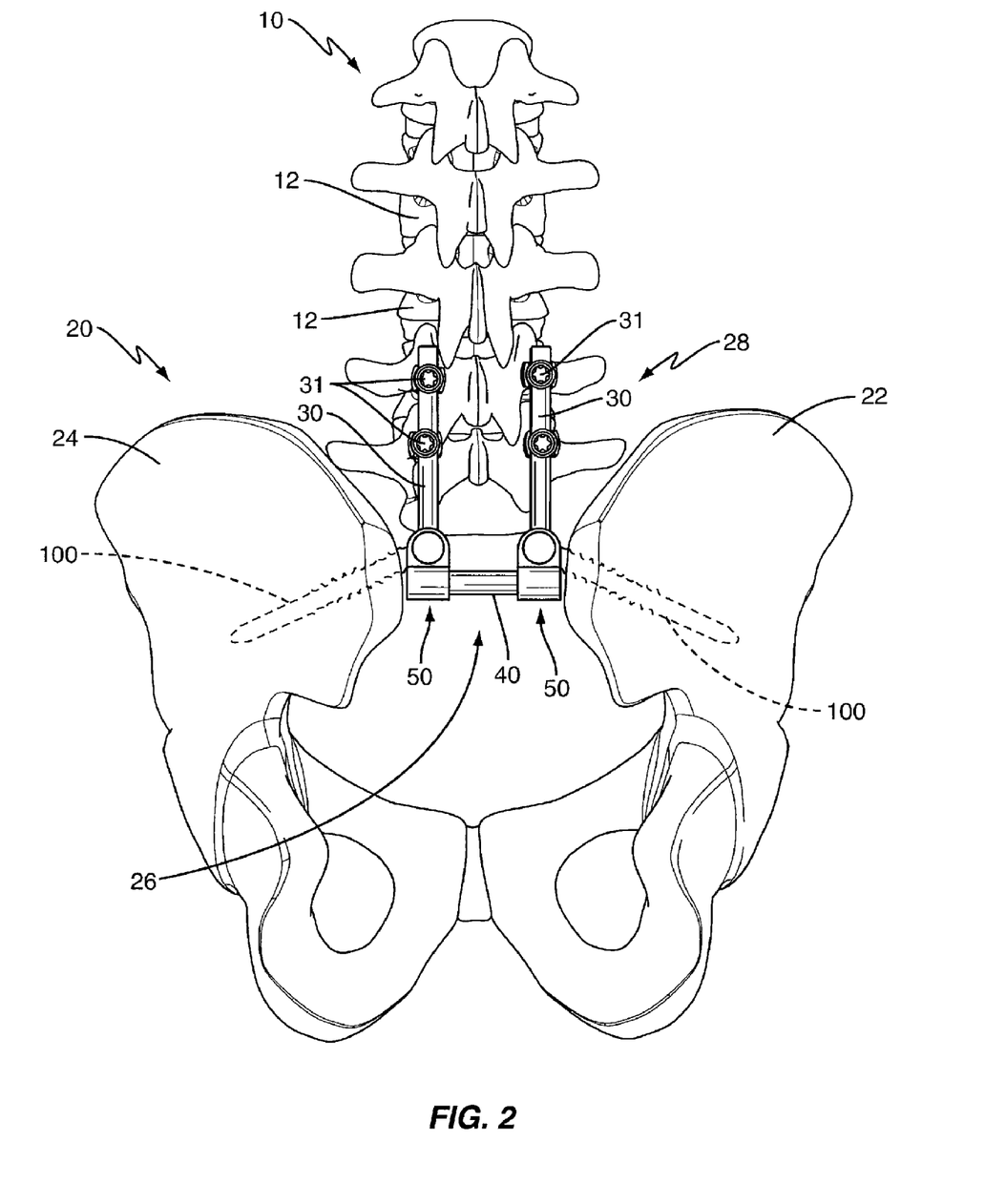
FIG. 2 shows a posterior view of one embodiment of a sacral reconstruction fixation construct.

One embodiment of a sacral reconstruction fixation construct is shown in FIG. 2, and generally indicated at 28. The construct of FIG. 2 includes a fixation device 50 that is simultaneously anchored to an ilium 22 or 24, fixed to a spinal rod 30, and fixed to a transiliac rod 40. The spinal rod 30 and fixation device 50 jointly vertically act to support the spinal column 10 from the ilium 22 or 24. The transiliac rod 40 and the fixation device 50 jointly act to stabilize the pelvic girdle 20 by holding the ilia 22,24 in fixed relative positions. Advantageously, the transiliac rod 40 is secured on each end by a fixation device 50, with each fixation device 50 anchored to a respective ilium 22 or 24 and to a respective a spinal rod 30. Thus, the fixation construct shown in FIG. 2 includes a transiliac rod 40, a right fixation device 50 anchored to a right ilium 22 and secured to a right spinal rod 30, and a left fixation device 50 anchored to a left ilium 24 and secured to a left spinal rod 30.

Figure 3:
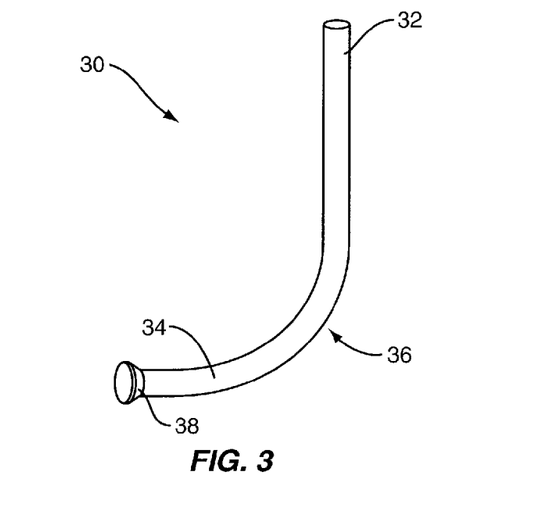
FIG. 3 shows one spinal rod embodiment suitable for use in the sacral reconstruction fixation construct of FIG. 2.

The spinal rods 30 are advantageously substantially similar. As such, only the right spinal rod 30 will be discussed; it being understood that the left spinal rod 30 is substantially similar. The spinal rod 30 may take the form of a L-shaped rod of generally constant outer diameter. The superior portion 32 of the spinal rod 30 is advantageously generally straight or slightly curved to follow the natural curve of the lower spine. The superior portion 32 joins to the inferior portion 34 proximate an approximately 90° bend 36. The inferior portion 34 is likewise advantageously generally straight or slightly curved. The distal end 38 of the spinal rod 30 is advantageously enlarged, such as being formed as a Morse taper. The spinal rod 30 may be a single unitary member, or may be formed in sections that are joined end to end. The spinal rod 30 may be made of any suitable material, such as 5.5 mm or 6.35 mm diameter titanium rod stock. The superior portion 32 of the spinal rod 30 is secured to the spinal column by suitable means. For example, the spinal rod 30 may be secured to the L4 and L5 vertebrae by suitable polyaxial pedicle screws 31.

The transiliac rod 40 may advantageously take the form of a straight, constant diameter rod of length suitable to extend from the left fixation device 50 to the right fixation device 50.

The transiliac rod 40 may be made of any suitable material, such as 5.5 mm or 6.35 mm diameter titanium rod stock.

Figure 4:
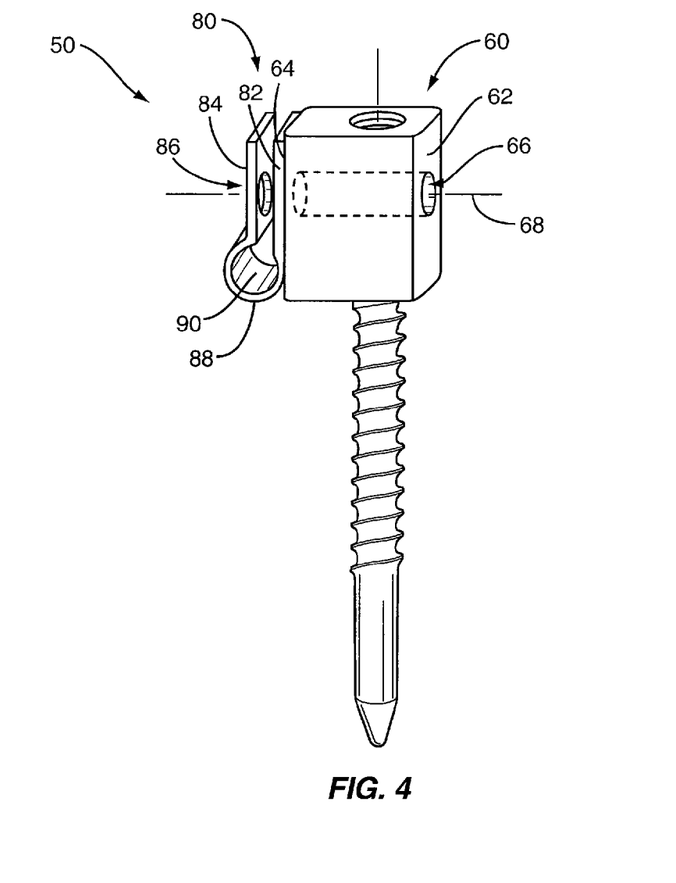
FIG. 4 shows one embodiment of a fixation device suitable for use in the sacral reconstruction fixation construct of FIG. 2.

One embodiment of a fixation device 50 is shown in FIGS. 2 and 4. The fixation device 50 generally includes a superior connector body 60, an inferior connector body 80, and an iliac screw 100. The superior connector body 60 may take the form of generally hollow cylindrical body. A rod-receiving passage 66 extends through the superior connector body 60 from the superior face 62 to the inferior face 64. This passage 66 is advantageously generally straight along axis 68, and is intended to receive the corresponding spinal rod 30. The superior connector body 60 may include an annular cavity 70 that opens to the inferior face 64, for reasons discussed further below. If desired, the inferior face 64 of the superior connector body 60 may include suitable surface texturing (e.g., small radial ridges/ribs, roughened texture, etc.) to aid in engaging the superior face of the inferior connector body 80, as discussed further below. The superior connector body 60 further includes locking elements 72,74 disposed on either side of axis 68 that are moveable relative to the remainder of the superior connector body 60. Locking element 72 typically takes the form of a set screw that may be driven toward axis when appropriate. Thus, locking element 72 is moveable between an initial position relatively farther from axis 68 and a locking position relatively closer to axis 68. Locking element 74 may take the form of an annular body with a generally spherically shaped side disposed toward iliac screw 100. Locking element 74 is moveable between an initial position relatively closer to axis 68 and a locking position relatively farther from axis 68. This locking element 74 is intended to be compressed between the spinal rod 30 and the head 102 of iliac screw 100 so as to fix the relative angle β between iliac screw 100 and axis 68, and thus the angular relationship between the iliac screw 100 and superior connector body 60. This locking element 74 functions similar to what is sometimes referred to as a "crown" in a polyaxial pedicle screw.

The inferior connector body 80 may take the form of a laterally oriented U-shaped element, with a superior end section 82, an inferior end section 84, and an intermediate lateral bridging section 88. The superior end section 82 may advantageously be relatively elongate and flat, with an aperture 86a therethrough about axis 68. A plurality of retention prongs 83 extend superiorly from the superior end section 82 into the annular cavity 70 of superior connector body 60. These retention prongs 83 may include suitable flanges/barbs to ensure that the inferior connector body 80 remains mated to the superior connector body 60. Further, the superior face of the inferior connector body 80 may include suitable surface texturing for engaging with the inferior face of the superior connector body 60 when the two are pressed together, as discussed further below. The inferior end section 84 is likewise advantageously relatively elongate and flat, with an aperture 86b therethrough about axis 68. This aperture 86b may be in the form of a tapered hole, as shown in the Figures. The combination of aperture 86a and aperture 86b together form a passage 86 that is disposed about axis 68. The intermediate lateral section 88 may advantageously take the form of a curvate section that forms a generally round passage 90 disposed transverse to axis 68. This passage 90 is intended to receive the transiliac rod 40. The passage 90 is variably sized such that it is relatively larger when the superior end section 82 and inferior end section 84 are spaced apart, and relatively smaller when superior end section 82 and inferior end section are pressed together 84.

The iliac screw 100 includes a head portion 102 and a shank portion 104 that extends from the head portion 102 along screw axis 108. The head portion 102 is advantageously generally spherical with a faceted central drive recess 103 disposed away from shank 104. The head portion 102 is configured to cooperate with a corresponding receiving chamber in superior connector body 60, and may be inserted into the chamber in a direction toward axis 68, and held mated to the superior connector body 60 by a suitable retaining ring 76 that forms an external boundary of the chamber. The shank portion 104 advantageously includes a threaded portion 105 disposed toward head portion 102, and an unthreaded portion 106 disposed distal from head portion 102. For additional information about this shank arrangement for an iliac screw, attention is directed to U.S. Pat. No. 5,643,264 to Sherman et al., which is incorporated herein by reference. The iliac screw 100 may advantageously be mated to the superior connector body 60 in a lockable polyaxial fashion, similar to a polyaxial pedicle screw. Thus, the shank portion 104 of iliac screw 100 may be disposed a wide variety of angular relationships with respect to axis 68 of superior connector body 60 until the polyaxial motion is locked down.

Figure 5:
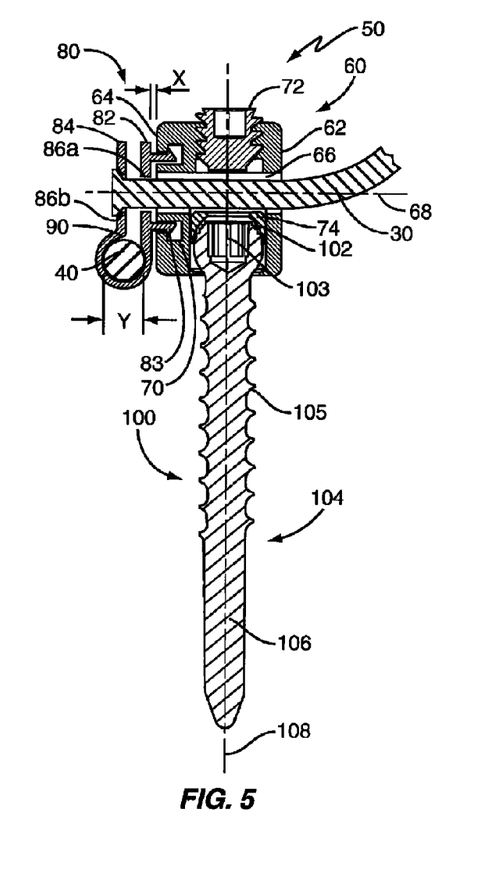
FIG. 5 shows a cross-section of the fixation device of FIG. 4 in the adjustable configuration.
Figure 6:
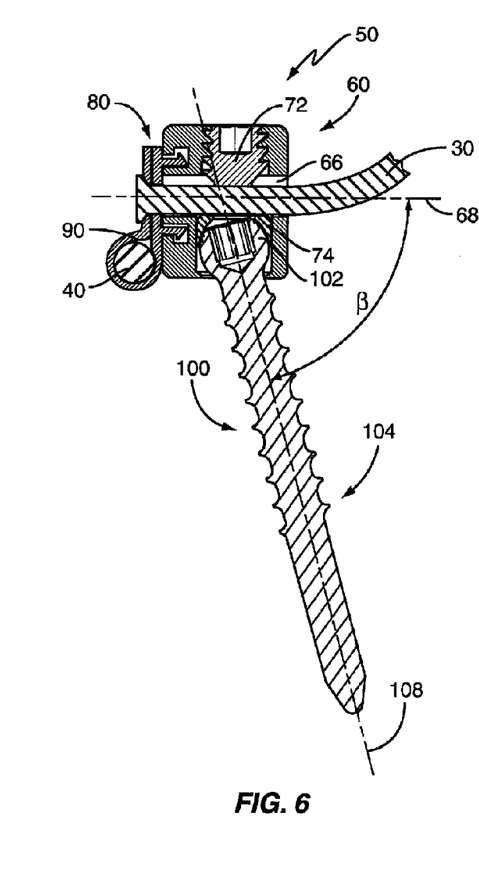
FIG. 6 shows a cross-section of the fixation device of FIG. 5 in the locked configuration.

The fixation device 50 may assume at least two different configurations. In a first configuration, referred to as the adjustable configuration, the superior connector body 60 and the inferior connector body 80 may be rotated relative to each other about axis 68. Further, the superior face of inferior connector body 80 is advantageously slightly spaced from the inferior face 64 of superior connector body 60 so as to form a gap X therebetween, and passage 90 of inferior connector body 80 is relatively larger in size. In order to allow gap X to be present, annular chamber 70 in superior connector body 60 may be suitably oversized relative to prongs 83 so as to allow some longitudinal displacement of inferior connector body 80 away from superior connector body 60 generally parallel to axis 68. In the second configuration, referred to herein as the locked configuration, the superior connector body 60 and inferior connector body 80 are prevented from rotating or being displaced relative to each other. Further, the superior end portion 82 and inferior end portion 84 of inferior connector body 80 are displaced toward each other, and advantageously touching, so that passage 90 is reduced in size from its size in the adjustable configuration. Also, the iliac screw 100 is angularly fixed relative to superior connector body 60 in the locked configuration.

Figure 7:
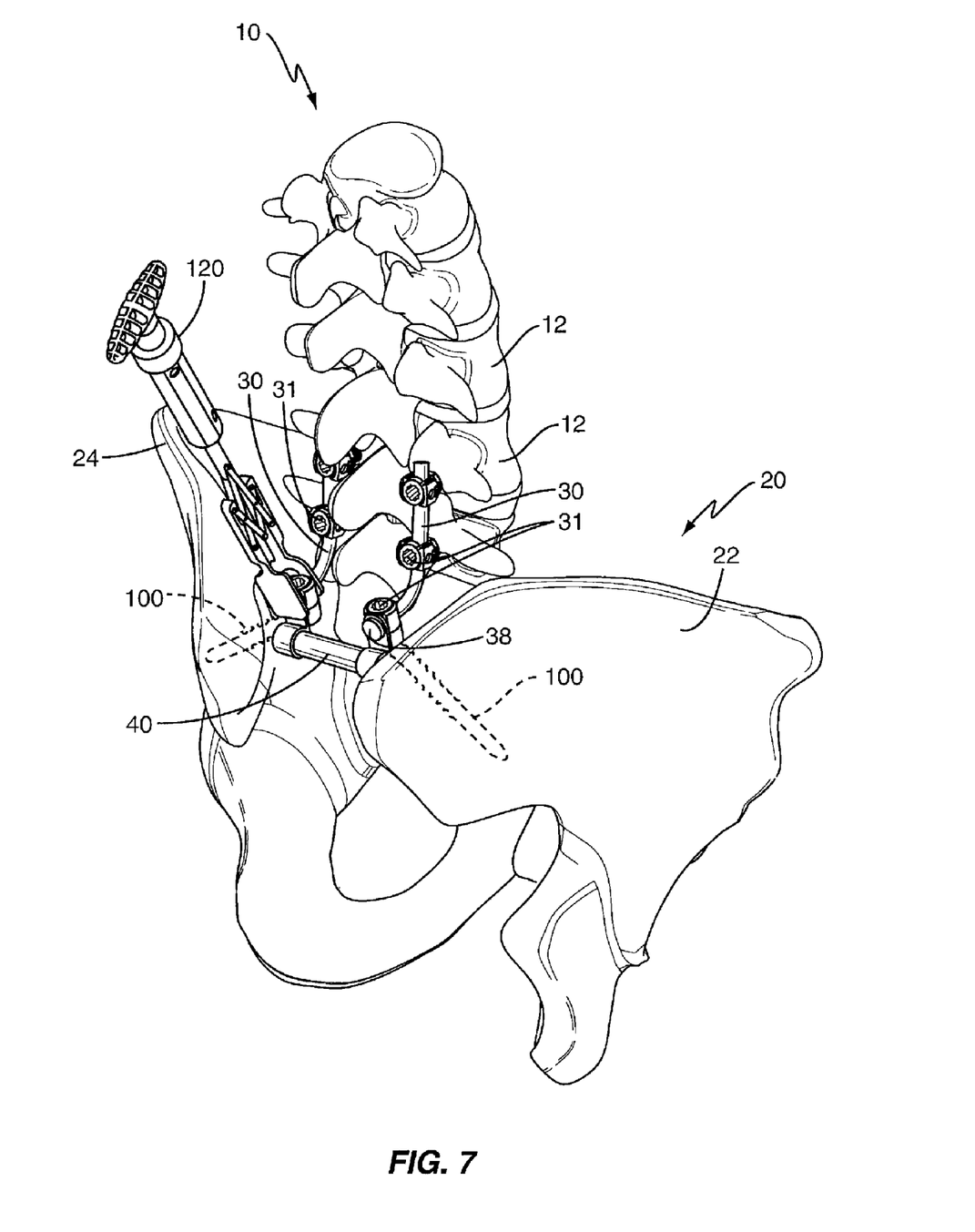
FIG. 7 shows a surgical tool applying a compressive force between the end of spinal rod and the superior face of the fixation device.

The sacral reconstruction fixation construct 28 of FIG. 2 is installed during a surgical procedure sometimes known as a sacrectomy. For this procedure, the surgeon prepares the surgical site and removes the sacrum 16 in a conventional fashion, typically using a combined anterior-posterior approach. See the article entitled "Surgical Treatment Of Primary Sacral Tumors: Complications Associated With Sacrectomy" by Dr. Mehmet Zileli et al., Neurosurgical Focus, volume 15, November 2003, which is incorporated herein by reference. Pedicle screws 31 are then attached to the relevant vertebrae 12 on each lateral side of the spinous process and initial pilot holes drilled in the ilia 22,24. A fixation device 50 is then anchored to each ilia 22,24 by driving the iliac screws 100 into the corresponding ilia 22,24. This may be achieved by removing the set screw 72 from the superior connector body 60 of the fixation device 50, and driving the iliac screw 100 via driving recess 103 in a fashion similar to seating a polyaxial pedicle screw. At this time, the fixation device 50 is in the adjustable configuration so that superior connector body 60 and inferior connector body 80 may be relatively rotated about axis 68. The relevant spinal rod 30 is then fed through passage 66 and passage 86 and up toward pedicle screws 31. The tapered end 38 of spinal rod 30 may engage the tapered aperture 86b in inferior connector body 80, but is not tightly held thereagainst at this time. The same procedure is repeated for anchoring the other fixation device 50 to the other ilium 24,22 and loosely connecting the same to the corresponding spinal rod 30. The transiliac rod 40 is then fed into the passages 66,86 of the respective fixation device 50. It should be noted that the ability of the inferior connector bodies 80 to rotate relative to their axis 68 helps facilitate the insertion of the transiliac rod 40. A surgical tool 120 is then used to press against the tapered end 38 of a given spinal rod 30 and the superior face 62 of superior connector body 60. This causes superior connector body 60 and inferior connector body 80 to be pressed together, locking down further relative rotation. The set screw 72 is then driven against the spinal rod 30 to clamp the spinal rod 30 between the set screw 72 and crown 74. This action also has the effect of locking down the polyaxial motion of iliac screw 100 relative to superior connector body 60 and therefore relative to spinal rod 30. The fixation device 50 is now in the locked configuration, with the inferior connector body 80 and superior connector body 60 relatively locked, the fixation device 50 fixed to spinal rod 30 and transiliac rod 40. The same procedure is then used on the other fixation device 50 to place it in the locked configuration. The surgical procedure then proceeds as appropriate, and the surgical site is closed.

The presence of the sacral reconstruction fixation construct 28 provides vertical support to the spinal column 10. In particular, the spinal column 10 is supported by the spinal rods 32 which are in turn supported by the ilia 22,24 via the fixation devices 50. Thus, the spinal column 10 is vertically supported by the pelvic girdle 20 via the sacral reconstruction fixation construct 28. In addition, the presence of the sacral reconstruction fixation construct 28 helps prevent the pelvic girdle 20 from collapsing. The transiliac rod 40 provides resistance against the two anchoring points (e.g., at iliac screws 100) moving toward or away from each other. Thus, the sacral reconstruction fixation construct 28 performs the dual functions of supporting the spinal column 10 and maintaining the pelvic girdle 20 against collapse. In addition, these two functions are provided by an easy-to-use device that is easily adaptable to various patient morphologies. As such, the surgical process is simplified. And, if the sacral reconstruction fixation construct is formed of radiolucent materials, such as PEEK or carbon fiber reinforced PEEK, the scatter artifacts typically seen with metallic implanted materials may be minimized in post-operative radiological studies. Thus, it may be advantageous to form the fixation device 50 out of radiolucent materials.

The discussion above has assumed that the spinal rod 30 engages the inferior connector body 80 sufficiently to prevent relative rotation of the inferior connector body 80 and superior connector body 60 by employing a Morse taper at spinal rod end 38. However, other approaches may be used for this purpose. For example, the enlarged distal tip 38 of the spinal rod 30 may include a plurality of splines (not shown) thereon, and aperture 86*b* in inferior connector body 80 may include corresponding splines. Further, the enlarged distal tip 38 of the spinal rod 30 may be formed as a separate section of the spinal rod 30, and then joined end to end with the remainder of the spinal rod 30, such as via a threaded connection or the like.

Figure 8:
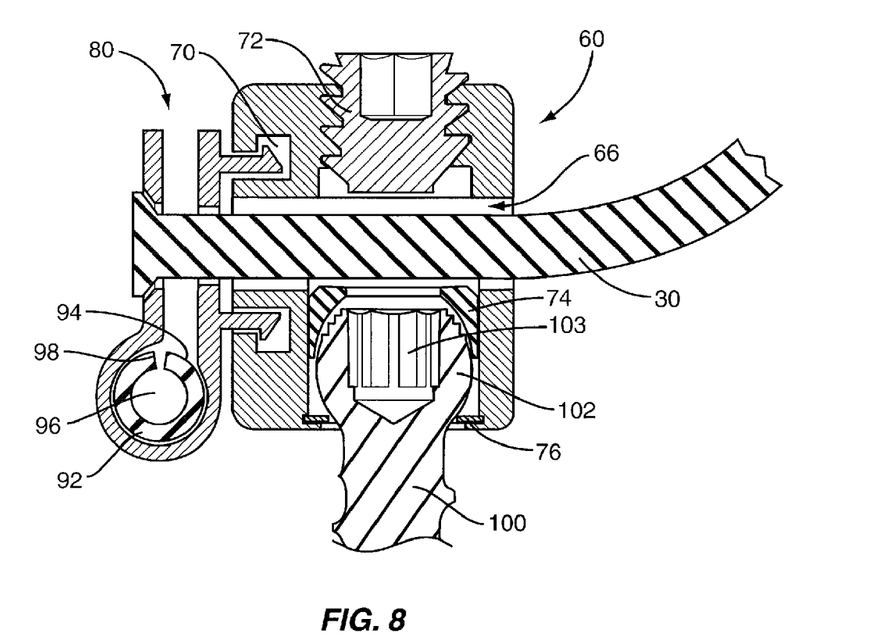
FIG. 8 shows a cross-section of another embodiment of a fixation device with a compressible insert for clamping the transiliac rod in the corresponding connector body.

The discussion above has also assumed that the transiliac rod 40 is directly clamped within passage 90. However, some embodiments of the fixation device 50 may alternatively use a compressible insert 92 disposed between the transiliac rod 40 and the interior wall of passage 90. For such embodiments, the compressible insert 92 may advantageously take the form of a convexly curved body 94 with a bore 96 therethrough. A slit 98 may be formed in the body 94 to allow the insert 90 to be compressed while maintaining its general shape. The interior wall of passage 90 may advantageously be correspondingly shaped, so that the compressible insert 92 may be rotated in multiple directions. With such an arrangement, urging inferior end portion 84 toward superior end portion 82 will tend to shrink passage 90, thereby compressing the insert 92, and thereby clamping the transiliac rod 40 in passage 90.

Figure 9:
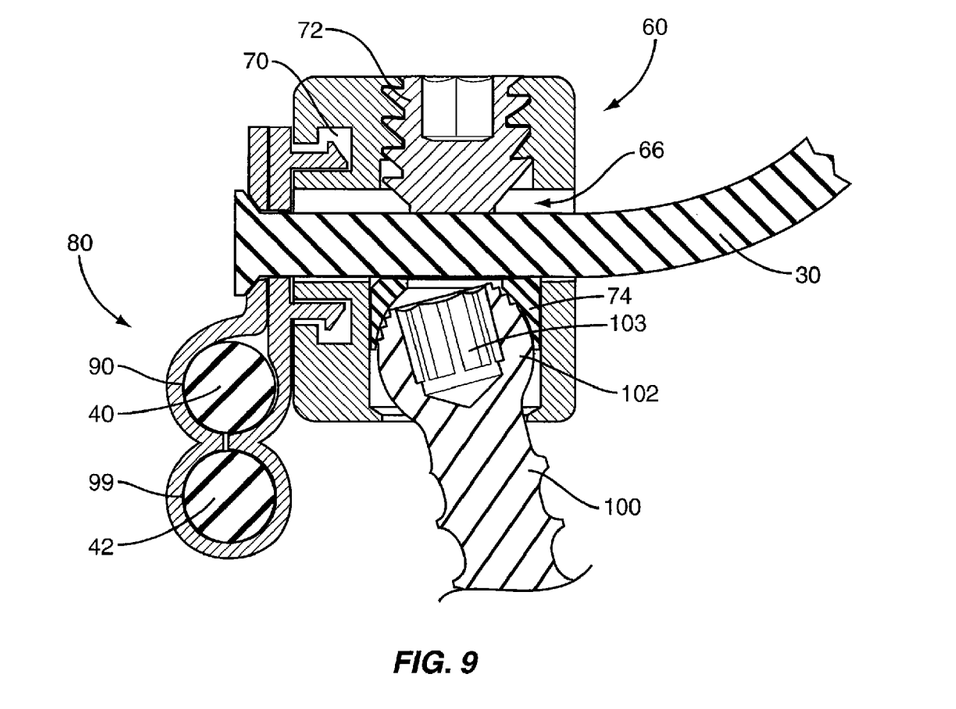
FIG. 9 shows a cross-section of another embodiment of a fixation device suitable for mating to multiple transiliac rods.

Further, some embodiments of the sacral reconstruction fixation construct 28 may employ multiple transiliac rods 40 disposed parallel to one another. For such embodiments, the inferior connector body 80 may be altered to provide an additional passage 99 of variable size that is oriented parallel to passage 90. It is intended that both of these passages 90,99 will assume their smaller size when the fixation device 50 is in its locked configuration. Further, as can appreciated, while the passages 90,99 are shown disposed on the same side relative to rod 30 in FIG. 9, the passages 90,99 may be alternatively be disposed on opposing sides of rod 30.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A sacral reconstruction fixation device, comprising:
a first connector body having a first rod-receiving passage therethrough along an axis;
an iliac anchor screw mated to said first connector body;
a second connector body distinct from said first connector body, but mated thereto; said second connector body having a rod-receiving first passage extending along said axis and a variably sized second passage disposed transverse to the axis;
one of the first and second connector bodies includes an extension and the other of the first and second connector bodies includes a chamber, the extension fits into the chamber with the extension being smaller than the chamber for the extension to be movable within the chamber, the extension and chamber being spaced from the first rod-receiving passage and the rod-receiving first passage with the first rod-receiving passage and the rod-receiving first passage being aligned when the extension is within the chamber;
wherein the fixation device is selectively configurable between:
a first adjustable configuration wherein the first and second connector bodies are coupled for relative rotation about said axis and the second passage is relatively larger; and
a second locked configuration wherein the first and second connector bodies are fixed against relative rotation and translation, said second passage is relatively smaller, and said iliac anchor screw is angularly fixed relative to said first connector body.

2. The sacral reconstruction fixation device of claim 1 wherein said iliac anchor screw connects to said first connector body so as to be lockably disposed at a variable angle relative to said axis.

3. The sacral reconstruction fixation device of claim 1 wherein said first connector body further comprises a first locking element disposed opposite to said iliac anchor screw relative to said axis and selectively displaceable toward said iliac anchor screw.

4. The sacral reconstruction fixation device of claim 1 wherein said first connector body further comprises a second locking element disposed between said iliac anchor screw and said axis and selectively engageable with said iliac anchor screw.

5. The sacral reconstruction fixation device of claim 1 wherein said second connector body further comprises a convexly curvate body disposed in said second passage; said convexly curvate body having a central bore therethrough of variable size.

6. The sacral reconstruction fixation device of claim 1 wherein said second connector body further comprises a third variably sized passage disposed generally parallel to said second passage; wherein the third passage is relatively larger when said fixation device is in said first configuration and relatively smaller when said fixation device is in said second locked configuration.

7. The sacral reconstruction fixation device of claim 1 wherein said second connector body further comprises the extension that extends superiorly into the chamber in said first connector body.

8. The sacral reconstruction fixation device of claim 7 wherein said chamber is an annular chamber.

9. The sacral reconstruction fixation device of claim 1 wherein an inferior entry into said first passage of said second connector body is tapered.

10. The sacral reconstruction fixation device of claim 1 wherein said first and second connector bodies are made from a radiolucent material.

11. A sacral reconstruction fixation assembly, comprising:
a first connector assembly comprising:
a first connector body having a first passage therethrough along an axis;
a first iliac anchor screw mated to said first connector body;
a second connector body distinct from said first connector body, but connected thereto; said second connector body having a rod-receiving first passage extending along said axis and a variably sized second passage disposed transverse to the axis;
a first spinal rod extending through both said first passages of said first connector body assembly;
the first and second connector bodies connected together by a connector spaced away from the first spinal rod;
a first transiliac rod disposed in said second passage;
wherein the first connector assembly is selectively configurable between:
a first adjustable configuration wherein the first and second connector bodies are coupled for relative rotation about said axis and the second passage is relatively larger; and
a second locked configuration wherein the first and second connector bodies are fixed against rotation and translation both relative to each other and relative to the spinal rod, said second passage is relatively smaller so as to clamp said transiliac rod therein to fix said second connector body against longitudinal translation along said transiliac rod, and the iliac anchor screw is angularly fixed relative to said first connector body.

12. The sacral reconstruction fixation device of claim 11 wherein said first iliac anchor screw connects to said first connector body of said first connector assembly so as to be lockably disposed at a variable angle relative to said first axis.

13. The sacral reconstruction fixation device of claim 11 wherein said first connector body of said first connector assembly further comprises a first locking element disposed opposite to said first iliac anchor screw relative to said first axis and selectively displaceable toward said first iliac anchor screw.

14. The sacral reconstruction fixation device of claim 11 wherein said second connector body of said first connector assembly further comprises a convexly curvate body disposed in its second passage; said convexly curvate body having a central bore therethrough of variable size.

15. The sacral reconstruction fixation device of claim 11 wherein said first spinal rod is generally L-shaped when viewed laterally.

16. The sacral reconstruction fixation device of claim 11 wherein an inferior end of said first spinal rod is enlarged.

17. The sacral reconstruction fixation device of claim 11 further comprising:
a second connector assembly comprising:
a first connector body having a first rod-receiving passage therethrough along a second axis;
a second iliac anchor screw mated to said first connector body;
a second connector body distinct from the corresponding first connector body, but mated thereto; said second connector body having a rod-receiving first passage extending along said second axis and a variably sized second passage disposed transverse to the axis;
a second spinal rod extending through both said first passages of said second connector assembly;
the first transiliac rod disposed in said second passage of said second connector assembly;
wherein the second connector assembly is selectively configurable between:
a first adjustable configuration wherein the second connector assembly first and second connector bodies are coupled for relative rotation about said second axis and the second connector assembly second passage is relatively larger; and
a second locked configuration wherein the second connector assembly first and second connector bodies are fixed against rotation and translation both relative to each other and relative to the second spinal rod, said second passage of said second connector body is relatively smaller so to clamp said transiliac rod therein to fix the corresponding second connector body against longitudinal translation along said transiliac rod, and the second iliac anchor screw is angularly fixed relative to its connector body.

18. The sacral reconstruction fixation device of claim 17 wherein said first connector assembly and said second connector assembly are substantially identical.

19. The sacral reconstruction fixation device of claim 17 wherein said second connector body of said first connector assembly further comprises a convexly curvate body disposed in the first connector assembly second passage; said convexly curvate body having a central bore therethrough of variable size.

20. The sacral reconstruction fixation device of claim 17 further comprising a second transiliac rod clamped to said first and second connector assemblies.

21. A sacral reconstruction surgical method, comprising:
resecting a sacrum;
providing a first connector assembly comprising:
a first connector body having a first rod-receiving passage therethrough along a first axis;
a second connector body distinct from said first connector body, but connected thereto; said second connector body having a rod-receiving first passage extending along said first axis and a variably sized second passage disposed transverse to the axis;

wherein the first connector assembly is selectively configurable between a first adjustable configuration and a second locked configuration;

wherein, in the first configuration, the first and second connector bodies are coupled for relative rotation about said axis and said second passage is relatively larger;

wherein, in the second configuration, the first and second connector bodies are fixed against relative rotation and translation, and the second passage is relatively smaller;

securing a first iliac screw to an ilium; said first iliac screw mated to said first connector body;

disposing an inferior portion of a first spinal rod in both said first passages of said first connector assembly after the first and second connector bodies are connected together;

securing a superior portion of the first spinal rod to a spinal column;

disposing a transiliac rod in said second passage with said first connector assembly in said first configuration;

thereafter causing said first connector assembly to assume said second configuration and thereby:

fixing the first and second connector bodies against rotation and translation both relative to each other and relative to the spinal rod; and clamping said transiliac rod in said second passage to fix said second connector body against longitudinal translation along said transiliac rod.

22. The method of claim 21 wherein the iliac anchor screw is angularly fixed relative to said first connector body when said first connector assembly is in said second configuration.

23. The method of claim 21 wherein moving said first connector assembly to said second configuration comprises moving a locking element associated with said first connector body to a locked position so as to clamp said first connector body to said spinal rod.

24. The method of claim 21 wherein said first connector assembly further comprises a convexly curvate body disposed in said second passage; said convexly curvate body having a central bore therethrough of variable size; said method further comprising:

disposing said transiliac rod in said central bore; and thereafter, decreasing a size of said central bore.

25. The method of claim 21 further comprising:

securing a superior portion of a second spinal rod to the spinal column;

providing a second connector assembly;

anchoring said second connector assembly to a complementary ilium via a second iliac screw;

fixing the second connector assembly to an inferior portion of the second spinal rod;

clamping the transiliac rod in the second connector assembly to fix said second connector assembly against longitudinal translation along said transiliac rod.

26. The method of claim 25 wherein said second connector assembly is substantially similar to said first connector assembly.

27. The method of claim 25 further comprising clamping a second transiliac rod to said first and second connector assemblies.

28. A sacrectomy method, comprising:

resecting a sacrum;

mounting a spinal rod to a spinal column;

mounting a fixation device to a first ilium via an iliac anchor screw; the fixation device comprising a first connector body and a second connector body mounted to the first connector body for selective rotation relative thereto;

fixing the spinal rod relative to the first ilium via the fixation device;

fixing a transiliac rod to the first ilium via the fixation device;

fixing the transiliac rod to a second ilium;

wherein said fixing the transiliac rod to the first ilium comprises locking the first connector body device against rotation relative to the second connector body and clamping the transiliac rod with the second connector body to affix the transiliac rod relative to the second connector body;

wherein said fixing the spinal rod relative to the first ilium comprises disposing the spinal rod through both said first and second connector bodies after the connector bodies are connected together and thereafter tightening a locking element to affix the first connector body relative to the spinal rod, both rotationally and longitudinally.

29. The method of claim 28 wherein said fixation device further comprises a convexly curvate body having a central bore therethrough of variable size; said method further comprising:

disposing the transiliac rod in the central bore; and thereafter, clamping the transiliac rod in the central bore.

30. The method of claim 28 wherein the step of fixing the transiliac rod to the second ilium comprising:

securing a superior portion of a second spinal rod to the spinal column;

providing a second fixation device;

anchoring said second fixation device to the second ilium via a second iliac screw;

fixing the second fixation device to an inferior portion of the second spinal rod;

clamping the transiliac rod in the second fixation device to fix said second fixation device against longitudinal translation along the transiliac rod.

31. The method of claim 30 wherein said second fixation device is substantially similar to said first fixation device.

32. The method of claim 30 further comprising clamping a second transiliac rod to said first and second fixation devices.

* * * * *